United States Patent [19]

Fleet et al.

[11] Patent Number: 4,999,360
[45] Date of Patent: Mar. 12, 1991

[54] METHOD OF INHIBITING VIRUS

[75] Inventors: George W. J. Fleet; Thomas W. Rademacher; Raymond A. Dwek, all of Oxford, United Kingdom

[73] Assignee: Monsanto Company, St. Louis, Mo.

[21] Appl. No.: 249,144

[22] Filed: Sep. 26, 1988

Related U.S. Application Data

[63] Continuation-in-part of Ser. No. 136,219, Dec. 21, 1987, abandoned.

[51] Int. Cl.$^5$ .......................................... A61K 31/445
[52] U.S. Cl. .................................................... 514/315
[58] Field of Search ........................................ 514/315

[56] References Cited

U.S. PATENT DOCUMENTS

| | | | |
|---|---|---|---|
| 4,065,562 | 12/1977 | Ohata et al. | 424/267 |
| 4,182,767 | 1/1980 | Morai et al. | 424/267 |
| 4,405,714 | 9/1983 | Kinast et al. | 546/242 X |

FOREIGN PATENT DOCUMENTS

87/03903 7/1987 PCT Int'l Appl.

OTHER PUBLICATIONS

Sunkara et al., Biochem. Biophys. Res. Commun. 148(1), 206–210 (1987).
Tyms et al., Lancet, Oct. 31, 1987, pp. 1025–1026.
Gruters et al., Nature, 74–77 (1987).
Fleet and Smith, Tetrahedron Lett. 26(11), 1469–1472 (1985).
Fleet and Smith, Tetrahedron 42(30), 5685–5692 (1984).
Fleet et al., Tetrahedron Lett. 26(26), 3127–3130 (1985).
Setoi et al., Chem. Pharm. Bull. 35(10), 3995–3999 (1987).
Chem. Absts. 106:50030 (1987).
Legler and Julish, Carbohyd. Res. 128, 61 (1984).
Fleet et al., Tetrahedron Lett. 25(36), 4029–4032 (1984).
Fleet et al., J. Chem. Soc. 13, 841–842 (1985).
Fung et al., Bio/Technology 5, 940–946 (1987).
Walker et al., Proc. Natl. Acad. Sci. USA 84, 8120–8124 (1987).
Karpas et al., Leuk. Res. 1, 35–49 (1987).
Karpas et al., Lancet, Jul. 18, 1987, pp. 132–133.
Karpas, Mol. Biol. Med. 1, 457–459 (1983).
Elbein, Ann. Rev. Biochem. 56, 497–534 (1987).
Elbein, Meth. Enzymol. 138, 661–709 (1987).
Fuhrmann, et al., Biochim. Biophys. Acta 825, 95–110 (1985).

*Primary Examiner*—Jerome D. Goldberg
*Attorney, Agent, or Firm*—Scott J. Meyer; James W. Williams, Jr.

[57] ABSTRACT

A group of five- and six-membered heterocyclic compounds having a nitrogen in the ring and 2 to 3 hydroxyl substituents on the ring are effective inhibitory agents of human immunodeficiency virus.

2 Claims, No Drawings

METHOD OF INHIBITING VIRUS

CROSS-REFERENCE TO RELATED APPLICATION

This is a continuation-in-part of copending application Ser. No. 136,219, filed Dec. 21, 1987, now abandoned.

BACKGROUND OF THE INVENTION

This invention relates to a method of inhibiting human immunodeficiency virus (HIV) and, more particularly, to five- and six-membered heterocyclic compounds having potential use for the treatment of acquired immune deficiency syndrome (AIDS).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., Science 224, 500-503 (1984), and Popovic et al., Ibid., 497-500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119-134 (1984)], while HIV-2 was more recently isolated by Montagnier and his coworkers in 1986 [*Nature* 326, 662 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426-432 (1988).

The first drug to be approved by the U.S. Food and Drug Administration (FDA) for treatment of AIDS was zidovudine, better known under its former name azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

More recently, certain glycosidase inhibitors have been tested for activity against the AIDS virus. Three such compounds suggested as potential anti-AIDS drugs are castanospermine, deoxynojirimycin (DNJ) and dihydroxymethyldihydroxypyrrolidine (DMDP). See, e.g., Sunkara et al., *Biochem. Biophys. Res. Commun.* 148(1), 206-210 (1987); Tyms et al., *Lancet*, Oct. 31, 1987; pp. 1025-1026.

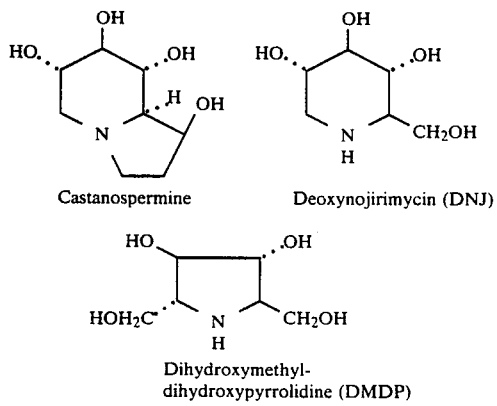

Castanospermine   Deoxynojirimycin (DNJ)

Dihydroxymethyl-dihydroxypyrrolidine (DMDP)

Thus, castanospermine, which is an alkaloid isolated from the seeds of Australian chestnut tree, has been found to interfere with normal glycosylation of HV virons, thereby altering the envelope glycoprotein and preventing entry of HIV into target cells. However, only a modest reduction in virion infectivity was found.

In PCT Inter. Appln. WO 87/03903, published July 2, 1987, the N-methyl derivative of deoxynojirimycin (DNJ) also was disclosed as having activity against HIV ostensibly based on its gluosidase I inhibitory activity. However, it was subsequently shown by Fleet et al., *FEBS Lett*, Vol. 237, pp. 128-132, 1988, that not all glucosidase I inhibitors are effective inhibitors of HIV. Therefore, some other mechanism may be responsible for HIV inhibitory activity.

DESCRIPTION OF THE INVENTION

In accordance with the present invention a group of five- and six-membered heterocyclic compounds having a nitrogen in the ring and 2 to 3 hydroxyl substituents on the ring have been found to have activity against the human immunodeficiency virus (HIV). As such, these compounds have potential use for the treatment of acquired immune deficiency syndrome (AIDS). The active compounds thus employed in the invention can be described structurally as derivatives of pyrrolidine or piperidine.

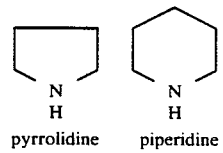

pyrrolidine   piperidine

Alternatively, they can be described by systemic chemical names as sugar derivatives in which the five-membered ring derivatives are considered as mimics of furanoses and the six-membered ring derivatives are considered mimics of pyranoses, with nitrogen instead of oxygen in the ring.

The effectiveness of the active compounds in the method of the invention has been demonstrated by positive inhibitory activity toward replication of the HIV in vitro. In accordance with this assay system, human T cells which are susceptible to HIV infection were used to visually determine the relative activity of test compounds to inhibit replication of the HIV infected cells.

Since various analogous compounds had substantially divergent results as described hereinafter, it is apparent that the effectiveness of any given compound as an inhibitor of HIV is unpredictable. Various theories have been proposed heretofore with respect to the effect of prior art HIV inhibitors. Research at several laboratories has established that interaction between the envelope glycoprotein, gp120, and some part of the CD4 antigen is involved in the recognition of HIV and most of the cells it infects and the binding of HIV to those cells. Thus, in one report which compared the positive effect of the glycosidase inhibitor deoxynojirimycin (DNJ) upon HIV infectivity against the absence of effect of the mannosidase I inhibitor deoxymannojirimycin (DMJ), which is the 2-epimer of DNJ, it was suggested that the perturbed carbohydrate structure of the gp120 or its precursor, imposed by the blocking of the N-linked oligosaccharide trimming pathway, is responsible for the effect. Gruters et al., *Nature* 330, 74–77 (1987).

The unpredictable effect of a test compound against HIV is demonstrated by several comparative studies of structurally analogous sugar derivatives. For example, while the known inhibition of the cytopathic effect (CPE) by the α-glucosidase I inhibitor castanospermine is confirmed, neither the epimer L-1,6-diepicastanospermine nor the stereoisomer of castanospermine, L-6-epicastanospermine, were found to be inhibitory. See Fleet et al., *FEBS Lett.*, Vol. 237, pp. 128–132, 1988.

So also, although both enantiomers of 1,4-dideoxy-1,4-imino-arabinitol are known glucosidase inhibitors [Fleet et al., *Tetrahedron Lett.* 26, 3127–3130(1985); Fleet et al., *Chemistry Lett.* 1051–1054(1986)], the L-enantiomer has strong HIV inhibitory activity whereas the D-enantiomer has very little effect on HIV replication. For both enantiomers, N-methylation reduced rather than increased anti-HIV activity. Neither the azofuranose analog of glucose nor the N-benzyl derivative were found to have an effect on CPE. Similarly, no HIV inhibition was observed for fagomine, the 2-deoxyglucose analog, although it too is known to have α-glycosidase inhibitory activity. See Fleet et al., *FEBS Lett.*, Vol. 237, pp. 128–132, 1988.

In order to delineate the chemical structures of the group of active inhibitory compounds employed in the method of the invention, these compounds can be conveniently broken down into several sub-groups as follows. In order to indicate stereoisomerism, solid and dotted lines show bonds directed above or below, respectively, the plane of the paper. The symbol Ph represents phenyl.

I. Five-Membered Rings

A. N-Methyl derivative of dihydroxymethyl-dihydroxypyrrolidine

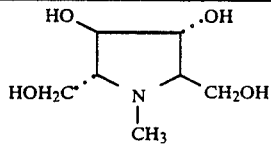

B. 1,4-Dideoxy-1,4-imino-L-arabinitol

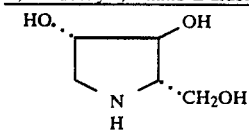

C. Stereoisomers of 1,4-dideoxy-1,4-imino-rib

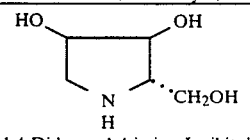

1,4-Dideoxy-1,4-imino-L-ribitol

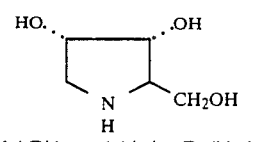

1,4-Dideoxy-1,4-imino-D-ribitol

D. N-Methyl derivatives of type B compounds

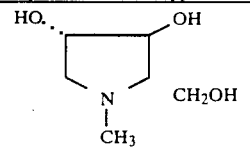

1,4-Dideoxy-1,4-imino-[N-methyl]-L-arabinitol

E. N-Substituted derivatives of type C compo

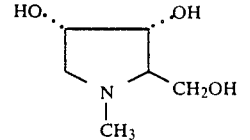

1,4-Dideoxy-1,4-imino-[N-methyl]-D-ribitol

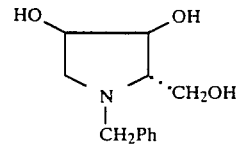

1,4-Dideoxy-1,4-benzylimino-L-ribitol

F. 1,4-Dideoxy-1,4-imino-D-talitol

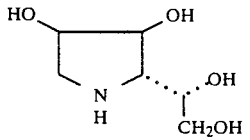

II. Six-Membered Rings

G. N-Methyl derivative of deoxymannojirimycin

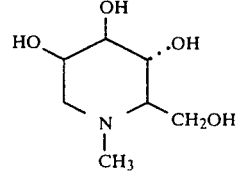

H. 1,5-Dideoxy-1,5-imino-L-fucitol derivatives

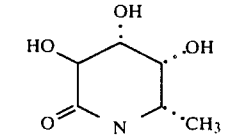

1,5-Dideoxy-1,5-imino-L-fuconolactam

J. N-Substituted 1,5-dideoxy-1,5-imino-L-fucitol derivatives

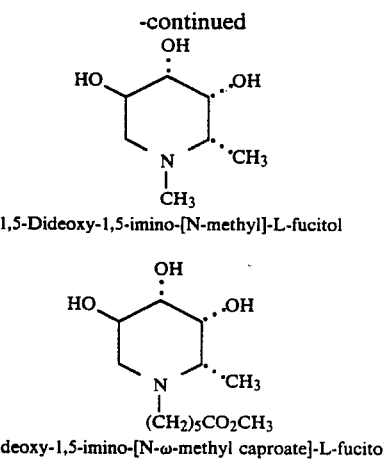

1,5-Dideoxy-1,5-imino-[N-methyl]-L-fucitol $$\text{1,5-Dideoxy-1,5-imino-[N-}\omega\text{-methyl caproate]-L-fucitol} \quad 12$$

Compounds 1, 5, 10, 11 and 12, above, are believed to be novel compounds.

The compounds employed in the method of this invention can be synthesized in accordance with general organic synthesis procedures set forth in the following examples. It will be appreciated that these compounds are not limited to the specific methods of preparation shown herein.

EXAMPLE 1

Compound 1 can be prepared by N-methylation of 2R,5R-dihydroxymethyl-3R,4R-dihydroxypyrrolidine (DMDP). The unambiguous enantiospecific synthesis of the latter compound is described by Fleet and Smith, *Tetrahedron Lett.* 26(11), 1469-1472 (1985). The N-methylation was carried out as follows: 30 mg of DMDP was dissolved in methanol (5 ml) and a catalytic amount of palladium black was added. The solution was stirred under H₂ for 5 minutes whereupon 46 μl of formaldehyde (37% in H₂O) was added. The reaction was stirred under hydrogen overnight. The reaction mixture was then filtered through a Celite® plug which was washed with 3×5 ml methanol. The solvents were removed under reduced pressure to yield a colorless oil which was purified by ion exchange chromatography to yield the N-methyl DMDP.

Compound 1 also can be synthesized from 2,5-dideoxy-2,5-imino-D-mannitol.

EXAMPLE 2

Compound 2 can be prepared by joining the C-1 and C-4 of xylose together with nitrogen to form the pyrrolidine ring as described by Fleet and Smith, *Tetrahedron* 42(30), 5685-5692 (1986), or from xylitol in which only hydroxyl groups from C-1 and C-4 of D-xylose are left unprotected as disclosed by Fleet et al., *Tetrahedron Lett.* 26 (26), 3127-3130 (1985).

Compound 2 also can be synthesized from D-mannose.

EXAMPLES 3 and 4

Compounds 3 and 4 can be synthesized in a series of steps from D-mannose and D-gulono-1,4-lactone, respectively. The preparation of compound 3 was carried out as follows and the synthesis of compound 4 was carried out in an analogous manner starting with D-gulono-1,4-lactone instead of D-mannose.

(a) 2,3:5,6-Di-O-isopropylidene-D-mannofuranose

To a suspension of D-(+)-mannose (12 g, 66.6 mmol) in acetone (200 ml), with vigorous stirring, was added conc. sulfuric acid (2.8 ml) at room temperature. After 3 hr., the reaction mixture was neutralized with anhydrous Na₂CO₃ (12g) filtered, and evaporated in vacuo to give the crude product as white solid, which was recrystallized from ethyl acetate-hexane (1:5) to afford the title acetonide (14 g, 81%) as white crystal. mp=124°-125° C. [lit., 124°-125° C.].

(b) 2,3:5,6-Di-O-isopropylidene-D-mannitol

To a stirred solution of NaBH₄ (567 mg, 15.0 mmol) in ethanol (30 ml) was added the above-prepared acetonide (3.9 g, 15.0 mmol) at room temperature. After 30 min., excess hydrides were hydrolyzed with excess NH₄Cl. Solvent was then evaporated in vacuo and the resulting residue was purified by flash chromatography (2:3, hexane-ethyl acetate) to afford the title diol (3.9g, quantitative) as white solid.
mp=47°-49° C. [α]$_D$20°=-9.2° (c, 1.05 in CHCl₃).

(c) 1,4-Bis(methanesulphonyl)-2,3:5,6-di-O-isopropylidene-D-mannitol

To the stirred diol prepared above (3.0 g, 11.5 mmo) in pyridine (20 ml) at 0° C. was added methanesulphonyl chloride (3.5 ml, 45.8) mmol followed by 4-dimethylaminopyridine (0.28 g, 2.3 mmol) was added. After 2 hr., pyridine was evaporated in vacuo and the residue was dissolved in CHCl₃ (100 ml). The solution was then washed with water (100 ml×2), dried (MgSO₄), filtered, and evaporated in vacuo to give the crude product as yellow oil, which was purified by flash chromatography (2:1 ethyl acetatehexane) to afford the title dimesyl compound (4.8 g, quantitative) as colorless syrupy oil. [α]$_D$20=+30.7° (c, 2.12 in CHCl₃).

(d) 2,3:5,6-Di-O-isopropylidene-1,4-dideoxy-1,4-benzylimino-D-talitol

The above-prepared dimesyl compound (4.8 g, 11.5 mmol) in benzylamine (10 ml) was stirred at 60°-70° C. for 60 hr. The mixture was then partitioned between brine (50 ml) and CHCL₃ (120 ml). The organic layer was separated, washed with water (100 ml×2) dried (MgSO₄), filtered, and evaporated in vacuo to give crude product as brown oil, which was purified by flash chromatography (2:3, ether-hexane) to afford the title cyclized product (2.7 g, 71%) as light yellow oil. [α]$_D$20=+60.1° (c, 1.65 in CHCl₃.

(e) 2,3:5,6-Di-O-isopropylidene-1,4-dideoxy-1,4-imino-D-talitol

The above-prepared cyclized compound (336 mg, 1.01 mmol) in ethanol (20 ml) was stirred under an atmosphere of hydrogen in the presence of 10% Pd/C (150 mg) at room temperature for 2 hr. The mixture was then filtered through celite and evaporated in vacuo to give crude product as solid, which was purified by flash chromatography (ethyl acetate) to afford the title acteonide product (233 mg, 95%) as white solid. The color of the product was changed to light yellow in the air.
mp=60° C. [α]$_D$20=-44.1° (c, 0.37 in CHCl₃).

(f) 1,4-Dideoxy-1,4-imino-D-talitol hydrochloride

The above-prepared acetonide (233 mg, 0.96 mmol, in 50% aqueous trifluoroacetic acid (10 ml) was stirred at room temperature for 15 hr. The solvent was then evaporated in vacuo to give product as white solid (trifluoroacetic acid salt), which was neutralized with dil. aqueous NaOH and purified by ion exchange chromatography (Dowex 50, 8-100, H$^+$ form, eluted with 0.5M aqueous ammonia) to afford the free amine as syrup. The free amine was dissolved in water (5 ml) and acidified to pH 4 with dilute aqueous hydrochloric acid. The solution was then freeze dried to afford the title compound (181 mg, 95%) as white solid.

mp=144°-145° C. $[\alpha]_D 20 = -56.3°$ (c, 0.41 in H$_2$O).

(g) 2,3-O-Isopropylidene-1,4-dideoxy-1,4-benzylimino-D-talitol

The cyclized compound as prepared in part (d) above (1.22 g, 3.66 mmol) in 80% aqueous acetic acid (20 ml) was stirred at 50° C. for 36 hr. The solvent was then evaporated in vacuo to give the crude product as light brown oil, which was purified by flash chromatography (ethyl acetate) to afford pure diol product (1.10 g, quantitative) as light yellow oil. $[\alpha]_D 20 = -15.2°$ (c, 1.22 in CHCl$_3$).

(h) 2,3-O-isopropylidene-1,4-dideoxy-1,4-benzylimino-L-ribitol

To the stirred diol prepared above (800 mg, 2.73 mmol) in 80% aqueous ethanol (20 ml) was added sodium periodate (1.75 g, 8.19 mmol) at room temperature. After 30 min., t.l.c. showed no starting material, sodium borohydride (207 mg, 5.46 mmol) was added to the reaction mixture and the stirring was continued for 1 hr. Excess hydrides were then hydrolized with solid NH$_4$Cl. The resulting mixture was filtered and evaporated in vacuo to give crude product as oil, which was purified by flash chromatography (8:3, ethyl acetate-hexane) to afford the pure alcohol product (557 mg, 78%) as light yellow oil. $[\alpha]_D 20 = +45.7°$ (c, 1.0 in CHCl$_3$).

(i) 1,4-Dideoxy-1,4-imino-L-ribitol hydrochloride

The above-prepared alcohol (257 mg, 0.98 mmol) in ethanol (10 ml) was stirred under an atmosphere of hydrogen in the presence of 10% Pd/C (120 mg) at room temperature. After 2 hr, the reaction mixture was filtered through celite and evaporated in vacuo to give the free amine as yellow solid (nmr showed no benzyl group), which was dissolved in 50% aqueous trifluoroacetic acid (6 ml) at room temperature. After 24 hr., evaporation of the solvent left crude product as light brown oil (trifluoracetic acid salt), which was neutralized with dilute aqueous NaOH and purified by ion exchange chromatography (Dowex 50X 8-100, H$^+$ form, eluted with 0.5M aqueous ammonia) to afford the free amine as yellow solid. The free amine was dissolved in water (5 ml) and acidified to pH 4 with dilute aqueous hydrochloric acid. The solution was then freeze dried to give the tite compound (165 mg, 76%) as light yellow solid.

mp=126°-131° C. $[\alpha]_D 20 = -59.0°$ (c, 0.59 in H$_2$O).

(j) 1,4-Dideoxy-1,4-benzylimino-D-talitol hydro-chloride

The cyclized compound as prepared in part (d) above (210 mg, 0.63 mmol) in 50% aqueous trifluoroacetic acid (10 ml) was stirred at room temperature. After 24 hr, solvent was evaporated in vacuo to give the tetraalcohol (trifluoroacetic acid salt) as oil, which was neutralized with dilute aqueous NaOH and purified by ion exchange chromatography (Dowex 50X 80-100, H$^+$ form, eluted with 0.5M aqueous ammonia) to afford the free amine as syrup. The syrup was dissolved in water (5 ml) and acidified to pH 4 with dilute aqueous hydrochloric acid. The solution was then freeze dried to give the title compound (164 mg, 90%) as very hygroscopic solid. $[\alpha]_D 20 = -10.1°$ (c, 0.94 in H$_2$O).

(k) 1,4-Dideoxy-1,4-benzylimino-L-ribitol

The alcohol as prepared in part (h) above (100 mg, 0.38 mmol) in 50% aqueous trifluoroacetic acid was stirred at room temperature. After 20 hr, evaporation of solvent left the product (trifluoroacetic acid) as brown oil, which was purified by ion exchange chromatography (Dowex 50X 8-100, H$^+$ form, eluted with 0.5M aqueous ammonia) to afford the title compound (76 mg, 90%) as light yellow solid (very hygroscopic). $[\alpha]_D 20 = +33.0°$ (c, 0.32 in H$_2$O).

In the analogous synthesis of the enantiomeric compound 4, the following corresponding products were prepared.

(a) 2,3:5,6-Di-O-isopropylidene-D-gulono-1,4-lactone. Recovered as colorless needle. mp=155° C. (from ethyl acetate). $[\alpha]_D 20 = -76.6°$ (c, 1.99 in CHCl$_3$). [lit., -67.8° (c, 4.16 in CHCl$_3$).

(b) 2,3:5,6-Di-O-isopropylidene-D-gulitol. Recovered as colorless needle. mp=73°-75° C. (from ether). $[\alpha]_D 20 = +11.3°$ (c, 1.80 in CHCl$_3$).

(c) 1,4-Bis(methanesulfonyl)-2,3:5,6-di-O-isopropylidene-D-gulitol. Recovered as colorless oil. $[\alpha]_D 20 = -7.3°$ (c, 1.82 in CHCl$_3$).

(d) 2,3:5,6-Di-O-isopropylidene-1,4-dideoxy-1,4-benzylimino-D-allitol. Recovered as light yellow oil. $[\alpha]_D 20 = -12.2°$ (c, 1.07 in CHCl$_3$).

(e) 2,3:5,6-Di-O-isopropylidene-1,4-dideoxy-1,4-imino-D-allitol. Recovered as light yellow oil. $[\alpha]_D 20 = +34.1°$ (c, 0.41 in CHCl$_3$).

(f) 1,4-Dideoxy-1,4-imino-D-allitol hydrochloride. Recovered as white solid. mp=110°-111° C. $[\alpha]_D 20 = +29.4°$ (c, 0.53 in H$_2$O).

(g) 2,3-O-Isopropylidene-1,4-dideoxy-1,4-benzylimino-D-allitol. Recovered as light yellow syrup. $[\alpha]_D 20 = -48.2°$ (c, 2.01 in CHCl$_3$).

(h) 2,3-O-Isopropylidene-1,4-dideoxy-1,4-benzylimino-D-ribitol. Recovered as light yellow oil. $[\alpha]_D 20 = -45.9°$ (c, 1.0 in CHCl$_3$).

(i) 1,4-Dideoxy-1,4-imino-D-ribitol hydrochloride. The free amine was recovered as a light brown solid. Upon dissolution in water and acidification with HCl followed by freeze drying of the solution, the hydrochloride salt was recovered as a light brown solid. mp=128°-132° C. $[\alpha]_D 20 = +57.6°$ (c, 0.59 in H$_2$O).

(j) 1,4-Dideoxy-1,4-benzylimino-D-allitol hydrochloride. Recovered as a very hygroscopic solid. $[\alpha]_D 20 = +23.1°$ (c, 0.72 in H$_2$O).

(k) 1,4-Dideoxy-1,4-benzylimino-D-ribitol. Recovered as a light yellow solid (very hygroscopic). $[\alpha]_D 20 = -37.3°$ (c, 0.49 in H$_2$O).

Synthesis of compound 3 from D-mannose is further described by Feet et al., *Tetrahedron* 44, 2649–2655(1988): synthesis of compound 4 from D-gulonolaotone is further described by Fleet and Son, *Tetrahedron* 44, 2637–2647(1988). Syntheses of compounds 3 and 4, respectively, also are disclosed by Setoi et al., *Chem. Pharm. Bull* 35(10), 3995–3999 (1987) and *Chem. Absts.* 106:50030 (1987).

EXAMPLES 5 and 6

Compounds 5 and 6 were prepared by N-methylation of Compounds 2 and 4, respectively, analogous to the method for the preparation of compound 1.

EXAMPLE 7

Compound 7 was prepared by N-benzylation of compound 3 as described in Example 3(k) above.

EXAMPLE 8

Compound 8 can be synthesized from D-mannose as described by Setoi et al., *Chem. Pharm. Bull.* 35(10), 3995–3999 (1987).

Syntheses of compounds 7 and 8 from D-mannose are further described by Fleet et al., *Tetrahedron* 44, 2649–2655(1988).

EXAMPLE 9

Compound 9 can be prepared by N-methylation of 1,5-dideoxy-1,5-imino-D-mannitol (deoxymannojirimycin or DMJ) analogous to the method for the preparation of compound 1. The synthesis of DMJ is described by Legler and Julish, *Carbohyd. Res.* 128, 61(1984); Fleet et al., *Tetrahedron Lett.* 25(36), 4029–4032(1984); and Fleet et al., *Ibid.* 29(23), 2871–2874(1988).

EXAMPLE 10

Compound 10 was synthesized in a series of steps from commercially available diacetone-D-allose (1,2:5,6-di-O-isopropylidene-α-D-allofuranose) as follows:

(a)
3-O-Benzyl-1,2:5,6-di-O-isopropylidene-α-D-furanose

Sodium hydride (50% dispersion in oil) (3.19 g, 66.3 mmol) was washed with distilled hexane (2×15 ml) under dry nitrogen, and suspended in dry THF (75 ml). Diacetone allose (15.93 g, 61.4 mmol) in dry THF (150 ml) was added over 1 hour. On completion, benzyl bromide (7.96 ml, 8.4 mmol) was added. The resulting mixture was stirred for three hours when t.l.c. (ethyl acetate/hexane 1:1) indicated no starting material (Rf0.2) and one product (Rf0.8). The reaction mixture was quenched with methanol (4 ml), diluted with ether (150 ml), filtered through a silica plug topped with celite and the filter cake washed with ether (3×75 ml). The solvent was removed and the crude yellow solid dissolved in dichloromethane (150 ml). The dichloromethane was washed with water (2×150 ml), dried (MgSO4), filtered and evaporated to a solid. Purification by recrystalization from hexane yielded the title benzyl ether (20.82 g, 95%) as a white solid, M.p. 65°–66° C., $[\alpha]_D20$ +105.6° (c, 0.25 in CHCl$_3$).

(b) 3-O-Benzyl-1,2-O-isopropylidene-α-D-allofuranose

The above-prepared benzyl ether (20.28 g, 57.94 mmol) was dissolved in 70% aqueous acetic acid (500 ml). The reaction was left for 15 hours, when t.l.c. (ethyl acetate/hexane 1:1) indicated no starting material (Rf 0.8) and one product (Rf 0.2). Evaporation of the solvent gave the crude product as a yellow syrup. Purification by flash column chromatography (ethyl acetate/hexane 3:1) yielded the diol (16.85 g, 94%) as a white crystalline solid, M.p. 63°–65° C. $[\alpha]_D20$ +119.4° (c, 0.25 in CHCl$_3$).

(c)
3-O-Benzyl-1,2-O-isopropylidene-6-O-p-toluene-sulphonyl-α-D-allofuranose

The above-prepared diol (13.91g, 44.8 mmol) was dissolved in dry pyridine (200 ml) and tosyl chloride (9.37g, 49.3 mmol) was added. The reaction was stirred at room temperature under dry nitrogen for 15 hours when t.l.c. (ethyl acetate/hexane 1:1) indicated unreacted starting material (Rf0.2) and two products (Rf0.6 and Rf0.7). The solvent was removed under reduced pressure and the crude product dissolved in dichloromethane (200 ml), washed with 100 ml aliquots of M HCl, brine and saturated sodium bicarbonate and dried (Na$_2$SO$_4$). The solvent was removed under reduced pressure and the crude product was purified by flash column chromatography (ethyl acetate/hexane 1:2) to yield 3-O-benzyl-1,2-O-isopropylidene-6-O-p-toluenesulphonyl-α-D-allofuranose (17.48 g, 84%) as a colorless oil. $[\alpha]_D20$ +51.4° (c, 0.97 in CHCl$_3$).

(d)
3-O-Benzyl-6-deoxy-1,2-O-isopropylidene-α-D-allofuranose

The above-prepared monotosylate (13.6 g, 29.3 mmol) was dissolved in dry THF (150 ml) under dry nitrogen. A 1 molar solution of "Superhydride" in THF (73.2 cm$^3$, 73.25 mmol) was added and the reaction stirred at room temperature for 1 hour when t.l.c. (ethyl acetate/hexane 1:1) indicated no starting material (Rf 0.6) and one product (Rf 0.5). The reaction was diluted with ethyl acetate (100 ml), washed with water (3×100 ml) and dried (Na$_2$SO$_4$). The solvent was removed under reduced pressure and the crude product purified by flash column chromatography (ethyl acetate/hexane 3:5) to yield 3-O-benzyl-6-deoxy-1,2-O-isopropylidene-α-allofuranose (10.8 g, 94%) as a colorless oil. $[\alpha]_D20$ +110.4° (c, 1.02 in CHCl$_3$).

(e)
5-Azido-3-O-benzyl-5,6-dideoxy-1,2-O-isopropylidene-β-L-talofuranose

The above-prepared alcohol (9.45 g, 31.85 mmol) was dissolved in dry pyridine (150 ml) and a catalytic amount of 4-dimethylaminopyridine was added. The reaction was cooled to 0° C. and methyl chloride (4.98 mls, 67.3 mmol) was added. The reaction was stirred under dry nitrogen and allowed to warm to room temperature over a period of 2 hours. A small sample of the reaction mixture was extracted and shaken with brine and diethyl ether, the organic layer was separated and t.l.c. (ethyl acetate/hexane 1:1) on this layer indicated no starting material (Rf 0.5) and one product (Rf 0.6). Diethyl ether (150 ml) was added to the reaction mixture, which was shaken with brine (3×150 ml). The organic layer was dried (Na$_2$SO$_4$) and the solvent removed under reduced pressure to yield the crude mesylate. The crude mesylate was immediately dissolved in dry DMF (150 ml) and sodium azide (6.25 g, 95.6 mmol) was added. The reaction was stirred at 70° C. for 3 hours when t.l.c. (ethyl acetate/hexane 1:3) indicated no starting material (Rf 0.6) and one product (Rf 0.7).

The solvent was removed, the crude product dissolved in water (150 ml) and extracted into dichloromethane (3×100 ml). The organic extracts were dried (MgSO$_4$) and the solvent removed under reduced pressure. The crude product was purified by flash column chromatography (ethyl acetate/hexane 1:5) to yield 5-azido-3-O-benzyl-5,6-dideoxy-1,2-O-isopropylidene-β-L-talofuranose (8.61 g, 84%). (Found C, 60.47; H, 6.84; N, 13.05%. C$_{16}$H$_{21}$O$_4$N$_3$ requires C, 60.18; H, 6.58; N, 13.16%). [α]$_D$20 +160.0° (c, 1.21 in CHCl$_3$).

(f) 5-Azido-3-O-benzyl-5,6-dideoxy-L-talonolactone

The above-prepared azide (2.39 g, 7.47 mmol) was dissolved in water/trifluoroacetic acid (50 ml, 2:3) and the reaction mixture was left for one hour when t.l.c. (ethyl acetate/hexane 1:3) revealed one product (Rf 0.3) and no starting material (Rf 0.7). The solvent was removed under reduced pressure to yield the crude lactol as an oil. This was dissolved in dioxan/water (50 ml, 2:1) and the solution was cooled to 0° C. Barium carbonate (4.97 g, 22.4 mmol) and bromine (1.94 ml, 22.4 mmol) were added and the reaction mixture stirred in the dark for six hours when t.l.c. (ethyl acetate/hexane 1:1) indicated one product (Rf 0.6) and no starting material Rf 0.4). Excess bromine was quenched by dropwise addition of sodium thiosulphate solution and the reaction mixture was centrifuged and decanted to remove liberated sulphur. The reaction mixture was diluted with ethyl acetate (50 ml) and the phases separated. The aqueous phase was washed with ethyl acetate (2×50 ml). The organic extracts were combined, dried (MgSO$_4$) and the solvent removed under reduced pressure. The crude product was purified by flash column chromatography (ethyl acetate/hexane 1:3) to yield 5-azido-3-O-benzyl-5,6-dideoxy-L-talonolactone (1.86 g, 78%) as a colorless oil which crystallized on standing. (Found: C, 56.37; H, 5.48; N, 14.36. C$_{13}$H$_{15}$O$_4$N$_3$ requires C, 56.41; H, 5.42; N, 14.60%). [α]$_D$20 +95.5° (c, 0.99 in CH$_2$Cl$_2$).

(g) 5-Azido-3-O-benzyl-5-deoxy-L-fuconolactone

The above-prepared lactone (1.86 g, 67.1 mmol) was dissolved in dry dichloromethane (100 ml), cooled to −30° C. and stirred under dry nitrogen. Pyridine (1.53 ml, 134.2 mmol) and trifluoromethanesulphonyl anhydride (1.84 ml, 73.8 mmol) were added. The reaction was stirred for 2 hours when t.l.c. (ethyl acetate/hexane 1:1) indicated no starting material (Rf 0.6) and one product (Rf 0.8). The reaction mixture was washed with 50 ml aliquots of water, 3% HCl, water, sat. sodium bicarbonate and water. Dry DMF (100 ml) was added and the majority of the dichloromethane was removed under reduced pressure. Sodium trifluoroacetate (3.969 g, 201 mmol) was added and the reaction was stirred under dry nitrogen for 15 hours when t.l.c. (ethyl acetate/hexane 1:3) indicated no starting material (Rf 0.6) and products (Rf 0.4 and Rf 0.5). The DMF was removed under reduced pressure and the product dissolved in dichloromethane (100 ml) which was washed with water (3×100 ml) and dried (MgSO$_4$). The solvent was removed under reduced pressure to yield a pale yellow oil. The impure product was heated in methanol/water (2:1) (100 ml) at 50° C. for 12 hours when t.l.c. (ethyl acetate/hexane 1:3) indicated only one product (Rf 0.4). The solvent was removed under reduced pressure and the crude product was purified by flash column chromatography (ethy acetate/hexane 1:3) to yield 5-azido-3-O-benzyl-5-deoxy-L-fuconolactone (1.51 g, 81%). [α]$_D$20 +171.6° (c, 1.49 in CH$_2$Cl$_2$).

(h) 3-O-Benzyl-1,5-dideoxy-1,5-imino-L-fuconolactam

The above-prepared fuconolactone (1.51 g, 55 mmol) was dissolved in ethyl acetate (50 ml) and a catalytic amount of palladium on carbon (5%) was added. The reaction was stirred under hydrogen for two hours when t.l.c. (ethyl acetate/hexane 1:3) indicated only baseline material and t.l.c. (ethanol/dichloromethane 1:9) indicated two products (Rf 0.5 and Rf 0.3). The reaction mixture was filtered through a celite plug which was washed with ethyl acetate (2×10 ml). The three portions were combined and the solvent removed under reduced pressure. The reaction mixture was dissolved in ethanol and left to stand for 12 hr when t.l.c. (ethanol/dichloromethane 1:9) indicated only one product (Rf 0.5). The solvent was removed under reduced pressure to yield the crude product as a white solid. Purification was by flash column chromatography (ethanol/dichloromethane 1:19) to yield 3-O-benzyl-1,5-dideoxy-1,5-imino-L-fuconolactam as a white solid (1.11 g, 81%). M.p. 191°–192° C. (Found: C, 62.17; H, 7.06; N, 5.45. C$_{13}$H$_{17}$O$_4$N requires C, 62.15; H, 6.77; N, 5.58%. [α]$_D$20 −70.3° (c, 0.90 in ethanol).

(i) 1,5-Dideoxy-1,5-imino-L-fuconolactam

Palladium black (15 mg) was prereduced by stirring in ethanol (25 ml) under hydrogen for 20 min. To the stirred solution a few drops of freshly prepared HCl/ethanol and a solution of the above-prepared benzyl protected lactam (1.11 g, 44 mmol) were added. The solution was stirred for 1 hour when t.l.c. (ethanol/dichloromethane 1:9) indicated one product (Rf 0.1) and no starting material (Rf 0.9). The solution was filtered through a celite plug and the solvent removed under reduced pressure to yield a colorless oil. This was recrystalized from water with acetone to yield 1,5-dideoxy-1,5-imino-L-fucononolactam (65 mg, 91%) as a white, crystalline solid, which melted with decomposition at 226°–227° C. (Found: C, 44.96; 7.12; N, 8.67. C$_6$H$_{11}$O$_4$N requires C, 44.72; H, 6.83; N, 8.69%). [α]$_D$20 −137.2° (c, 0.83 in H$_2$O).

(j) 1,5-Dideoxy-1,5-imino-L-fucitol

The benzyl protected lactam prepared in part (h), above, was used also to synthesize 1,5-dideoxy-1,5-imino-L-fucitol by first converting to the protected amine, 3-O-benzyl-1,5-dideoxy-1,5-imino-L-fucitol, and then removing the 3-O-benzyl group as in part (i), above. The title compound was recovered as a colorless oil. (Found C, 48.76° C.; H, 8.82%; N, 9,30%. C$_6$H$_{13}$NO$_3$N requires C, 48.98; H, 8.84; N, 9.52%). [α]$_D$20 −49° (c, 0.78 in H$_2$O).

Synthesis of Compound 10, also referred to as L-fuconic-δ-lactam, from glucose is described by Fleet et al., *J. Chem. Soc. Chem. Commun.*, pp. 483–485 (1988).

EXAMPLES 11 and 12

Compounds 11 and 12 can be synthesized from 1,5-dideoxy-1,5-imino-L-fucitol. The synthesis of the latter compound from commercially available methyl α-D-glucopyranoside is described by Fleet et al., *J. Chem. Soc.* 13, 841–842 (1985). The specific synthesis of compounds 11 and 12 was as follows:

1,5-Dideoxy-1,5-imino-[N-methyl]-L-fucitol 1,5-Dideoxy-1,5-imino-L-fucitol (90 mg, 0.61 mmol) was dissolved in 80% aqueous methanol (3 ml). Palladium black (50 mg) was added and the flask evacuated and filled with hydrogen. Formaldehyde (100 μl, 37%) was added through a septum and the mixture stirred magnetically overnight. The catalyst was filtered off and the title compound isolated from a Dowex® 50 (H+) ion exchange column by eluting with 1M ammonium hydroxide solution. After evaporation and freeze-drying the isolated yield was 50 mg, 52%. The product crystallized from methanol/chloroform $[\alpha]_D 20$ +12.8 (c, 0.18, CHCl$_3$).

Found: C 52.01, H 9.51, N 9.00; calculated C$_7$H$_{15}$NO$_3$, C 52.15, H 9.38, N 8.69.

1,5-Dideoxy-1,5-imino-[N-ω-methyl caproate]-L-fucitol 1,5-Dideoxy-1,5-imino-L-fucitol (147 mg, 1 mmol) was dissolved in methanol (1.6 ml), water (0.4 ml) and acetic acid (0.09 ml) in a r. b. flask. Palladium black (100 mg) and methyl 6-oxohexanoate (0.2 ml) were added. The flask was evacuated while stirring magnetically and hydrogen introduced and the reaction stirred overnight. T.l.c. (ethanol/methanol/1M NH$_4$OH, 2:2:1) showed a complete reaction of the starting material, Rf 0.23, and one product, Rf 0.72. The mixture was filtered through a cotton plug directly onto a small Dowex® 50 ion exchange resin column (H+ form) and washed with water and methanol. The free amine form of the title compound was converted to the HCl salt form by eluting the product off the column with 0.5M methanolic HCl (about 40–50 ml). The fractions containing the product were combined and the solvent was removed by evaporation of the product to dryness on a rotary evaporator. Yield of the HCl salt form of compound 12, 250 mg, 80%.

EXAMPLE 13

The inhibitory activity of the compounds of this invention toward HIV is demonstrated by an in vitro assay system in which T-cells are grown in suitable nutrient culture medium and exposed to HIV inoculum in the presence or absence of test compound and compared with control cells which are grown in culture medium alone. After a suitable period of incubation, the cultures are scored for the presence of so-called syncytial cells (giant cells). Typical examples of such a test for the evaluation of inhibitors of HIV have been disclosed by Fung et al., *Bio/Technology* 5, 940–946 (1987); Tyms et al., *Lancet*, Oct. 31, 1987, pp. 1025–1026; Gruters et al., *Nature* 330, 74–77 (1987); and Walker et al., *Proc. Natl. Acad. Sci. USA* 84, 8120–8124 (1987).

In the present case, a human leukemic T-cell line was used which is described by Karpas, *Leuk. Res.* 1, 35–49 (1977). These cells were seeded into microtiter wells at a concentration of $5 \times 10^3$ cells per 0.2 ml of culture medium in each well. RPMI-1640 supplemented with 10% fetal calf serum was used as the culture medium. Each of the test compounds was added to either 4 or 6 wells of the microtiter plate. Two or three of the wells were infected with about $10^3$ HIV-1 particles per well and two or three other wells were similarly infected with HIV-2 particles. During the following 3 weeks, with a twice weekly change of medium containing the corresponding test compounds, the infected cells were monitored for the appearance of syncytial formations (giant cells) and eventual cytopathic effect (CPE). The non-infected cells were monitored for the possible cytotoxic effect of the test compounds. Likewise, the rate of growth was estimated in relation to growth of the control cells. The cultures were scored on a scale from 0 to 4+ by microscopic examination on the following basis:

0 = complete CPE
± = most cells dead
1+ = about ¼ of cells alive
2+ = about ½ of cells alive
3+ = about ¾ of cells alive
4+ = all cells appear alive The following Table I summarizes the results of the foregoing active compounds.

TABLE I

| Test Compound | Compound Concentration mg/ml | T-cells HIV-infected | T-cells Control |
|---|---|---|---|
| 1 | 0.1 | 1+ | 4+ |
| 2 | 0.3 | 4+ | 4+ |
| 3 | 0.13 | 1+ | 4+ |
| 4 | 0.13 | 2+ | 4+ |
| 5 | 0.1 | 1+ | 4+ |
| 6 | 0.1 | 1+ | 4+ |
| 7 | 0.1 | 1+ | 4+ |
| 8 | 0.16 | 1+ | 4+ |
| 9 | 0.3 | 1+ | 4+ |
| 10 | 0.1 | 1+ | 4+ |
| 11 | 0.1 | 1+ | 4+ |
| 12 | 0.03 | 1+ | 4+ |

By way of comparison, in the same test protocol, AZT is toxic at 0.01 micrograms per ml. The unpredictable effectiveness of any given compound as an inhibitor of HIV and, thereby, the unobviousness of the invention was demonstrated by: (A) the above positive inhibitory results with 1,4-dideoxy-1,4-benzylimino-L-ribitol (compound 7) whereas the enantiomer 1,4-dideoxy-1,4-benzylimino-D-ribitol [prepared in Example 4(k)] was inactive in the above test protocol (scored as zero); and (B) the above positive inhibitory results with 1,5-dideoxy-1,5-imino-L-fuconolactam (compound 10) whereas the corresponding 1,5-dideoxy-1,5-imino-L-fucitol [prepared in Example 10(j)] was inactive in the above test protocol (scored as zero.)

EXAMPLE 14

Further testing of compounds 1 to 12 for inhibition of HIV replication was carried out to confirm the results of Example 13. To discriminate between specific anti-HIV activity and cytotoxicity, the effects of these compounds on HIV infected and non-infected T-lymphocytes were assessed in parallel. Using the T-cell line and cell free suspensions of HIV prepared from infected cultures, as in Example 13, the concentration of infectious particles (TCID, tissue culture infectious dose) was estimated using an end-point titration where the number of infectious HIV particles in each preparation was determined by the highest dilution which contained infectious HIV, as detected by syncytial formation, cytotoxicity and HIV antigen synthesis after 10 days of culture with $10^4$ T-45 cells. Stock solutions of all compounds were prepared by dissolving each compound at a concentration of 1 mg/ml in growth medium. These solutions were filtered and sterilized (0.22 μm). Initially, each compound was tested at concentrations of 0.1 mg/ml and 0.5 mg/ml. If a given compound showed inhibition of HIV replication without cytotoxicity the assay was repeated with greater dilutions or, if it showed partial inhibition, with higher concentrations.

The following Table II sets forth the cytotoxic activity (% cell death) and the anti-HIV activity (% cytopathic effect, CPE, reduction), for these compounds.

TABLE II

| Test Compound | Compound Dosage (mg/ml) | Cytotoxic Activity (% cell death) | Anti-HIV Activity (% CPE reduction) |
| --- | --- | --- | --- |
| 1 | 0.1 | 0 | 25 |
| 2 | 0.1, 0.5 | 0, 0 | 50, 100 |
| 3 | 0.13 | 0 | 25 |
| 4 | 0.13 | 0 | 50 |
| 5 | 0.1 | 0 | 25 |
| 6 | 0.1 | 0 | 25 |
| 7 | 0.1 | 0 | 25 |
| 8 | 0.16 | 0 | 25 |
| 9 | 0.3 | 0 | 25 |
| 10 | 0.10 | 25 | 50 |
| 11 | 0.1 | 0 | 25 |
| 12* | 0.10, 0.25 | 0, 0 | 75, 90 |

*Tested in both free amine and HCl salt forms with similar results.

The antiviral agents described herein can be used for administration to patients infected with the human immunodeficiency virus by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, PA.

Various other examples will be apparent to the person skilled in the art after reading the present disclosure without departing from the spirit and scope of the invention. It is intended that all such further examples be included within the scope of the appended claims.

What is claimed is:

1. The method of inhibiting human immunodeficiency virus in a patient infected with said virus comprising administering to said patient a virally inhibitory effective amount to inhibit HIV of a compound selected from the group consisting of
   (a) 1,5-dideoxy-1,5-imino-L-fuconolactam,
   (b) 1,5-dideoxy-1,5-imino-[N-methyl]-L-fucitol,
   (c) 1,5-dideoxy-1,5-imino-[N-ω-methyl caproate]-L-fucitol,
   and their pharmaceutically acceptable salts.

2. The method of claim 1 in which the inhibitor compound is 1,5-dideoxy-1,5-imino-[N-ω-methyl caproate]-L-fucitol.

* * * * *